United States Patent [19]
Jacobson et al.

[11] Patent Number: 5,296,640
[45] Date of Patent: Mar. 22, 1994

[54] PROCESS FOR PREPARING PERHALOACYL CHLORIDES

[75] Inventors: Stephen E. Jacobson, Princeton Junction, N.J.; Wayne B. Ely, Chadds Ford, Pa.

[73] Assignee: E. I. Du Pont de Nemours and Company, Wilmington, Del.

[21] Appl. No.: 945,055

[22] Filed: Sep. 15, 1992

[51] Int. Cl.$^5$ .................... C07C 51/16; C07C 51/21; C07C 51/215

[52] U.S. Cl. .................................. 562/856; 562/859; 562/861; 562/863

[58] Field of Search ............. 562/859, 860, 863

[56] References Cited

U.S. PATENT DOCUMENTS 3,288,850  11/1966  Nychka .............................. 562/605
3,894,082  7/1975  Fernschild et al. .................. 562/605
5,041,647  8/1991  Gotoh et al. ........................ 562/859

FOREIGN PATENT DOCUMENTS 1017490  8/1964  United Kingdom .

OTHER PUBLICATIONS

Streitwieser, Andrew and Heathcock, Clayton H., "Introduction to Organic Chemistry," 1976, pp. 78 and 74.

*Primary Examiner*—José G. Dees
*Assistant Examiner*—Dwayne C. Jones

[57] ABSTRACT

A process for preparing perhaloacyl chlorides such as trifluoroacetyl chloride by oxidizing lower perfluoroalkyl and monochloroperfluoroalkyl dichloromethane within the supercritical region and in the absence of water.

6 Claims, No Drawings

PROCESS FOR PREPARING PERHALOACYL CHLORIDES

FIELD OF THE INVENTION

This invention relates to a process for preparing perhaloacyl chlorides, for example, trifluoroacetyl chloride. More especially this invention relates to the oxidation of lower perfluoroalkyl and monochloroperfluoroalkyl dichloromethanes within the supercritical region and in the absence of water. The reaction is of a general nature for the preparation of related perhaloalkyl acid chlorides.

DESCRIPTION OF THE RELATED ART

Trifluoroacetyl Chloride (TFAC) is useful as a starting material for the production of agricultural chemicals and pharmaceuticals, since as the acid chloride it readily reacts with compounds containing amines or alcohols to produce amides and esters, respectively. There are a number of routes in the literature for the production of TFAC each having certain limitations.

For example, a process for the oxidation of 1,1-dichloro-2,2,2-trifluoroethane (HCFC-123) with oxygen in the presence of water is disclosed in U.S. Pat. No. 5,041,647. In that patent it is stated that the water is necessary as a catalyst and that in the absence of water the oxidation of HCFC-123 hardly takes place. "Perfect mixing" is required to prevent local heating, i.e., hot spots. In that process a mixture of TFAC and trifluoroacetic acid (TFAA) is always formed. It is difficult to separate the mixture of water, TFAC, and TFAA and an object of that patent is the further hydrolysis of the residual TFAC with water at elevated temperatures and pressures to produce TFAA.

U.S. Pat. No. 3,883,407 discloses a process wherein TFAC is produced by reacting HCFC-123 with oxygen in the presence of active radiation. Photochemical processes such as those described in that patent usually require high investment.

SUMMARY OF THE INVENTION

This invention is a process for preparing perhaloacyl chlorides of the formula $X(CF_2)_nCOCl$ comprising contacting compounds of formula $X(CF_2)_nCHCl_2$ with oxygen within the supercritical region of the compounds
wherein
X=F or Cl and
n=1–4.

DETAILED DESCRIPTION OF THE INVENTION

An object of the present invention is to prepare perhaloacyl chlorides by the oxidation of perfluoroalkyl and monochloroperfluoroalkyl dichloromethanes. This improved process exhibits increased selectivity and conversion in comparison to the thermal process of the prior art. This is accomplished by contacting the starting material with oxygen within the supercritical region of the reactants to produce products according to the following general equation:

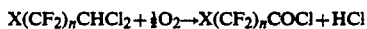

$$X(CF_2)_nCHCl_2 + \tfrac{1}{2}O_2 \rightarrow X(CF_2)_nCOCl + HCl$$

wherein
X=F or Cl and
n=1–4.

The "critical point" is the set of physical conditions, i.e., temperature and pressure at which the density and other physical properties of the liquid and vapor become identical. Any temperature and pressure at or above the critical point is defined as the "supercritical region". Under these conditions (at or above the critical point) "perfect mixing" is not important. "In the absence of water" is referred to herein to water found in commercial quantities of starting materials.

This reaction may be carried out either in a batch or continuous fashion. In each case conditions which are not in the explosive range for the mixture of oxygen and the material to be oxidized are preferred. This is generally accomplished by using air as the oxidizing material. Excessive drying of the air is not required as traces of water (e.g., quantities typically found in commercial quantities of starting material of <500 ppm) neither inhibit nor catalyze the reaction to any significant extent.

Although any practical ratio of oxygen can be employed, preferably the mole ratio of oxygen to the material to be oxidized can range from 0.5 to 1, with a ratio of about 0.75 being more preferred. Ratios above 1 are more likely to fall within the explosive range and may require higher reaction temperatures. Ratios below 0.5 will require the recycle of large amounts of unreacted lower perfluoroalkyl and monochloroperfluoroalkyl dichloromethanes. The oxygen is normally diluted with an inert gas so as to keep the reaction mixture out of the explosive range and to avoid exotherms which could decompose the product perhaloacyl chloride. The use of dry air is preferred.

A reactor which will not be seriously corroded by small amounts of reaction by-products such as hydrogen fluoride, as well as chlorine and water which can come from the reaction of hydrogen chloride and oxygen, is required.

Materials useful for the reactor surfaces include silver, nickel, tantalum, nickel based alloys sold under the trademarks HASTELLOY®, INCONEL®, and the like. Stainless steel such as 316 is unsatisfactory as it causes many by-products to be produced and its use results in decreased selectivity and conversions. Glass is severely etched and therefore not practical. ALLOY C276 sold under the trademark HASTELLOY® C276 and ALLOY 600 sold under the trademark INCONEL® 600 are the preferred reactor materials since they show minimum corrosion and selectivity of TFAC is consistently high.

The major parameters for carrying out the reaction are temperature, pressure, and time. The higher the temperature or pressure, the shorter the time required to get optimum conversions. The reaction may be carried out in a temperature range of 190°–320° C. and at pressures from 400–1500 psig. Temperatures of 220°–300° C. and pressures of 700–1400 psig are preferred. At temperatures and pressures below the preferred range the reaction is slow and the conversions are lower. At temperatures above the preferred range, the reaction conditions must be carefully controlled to avoid side reactions which lower the selectivity to TFAC. Pressures above the preferred range may be employed but the equipment costs would be higher. However the reaction can be run at the higher temperatures by use of much shorter reaction times. Exemplification of suitable reaction times is provided hereinafter. Selection of time is subject to the reaction variables which a skilled artisan can readily select. It will be appreciated by those skilled in the art that optimum conditions will also depend on the nature of the lower perfluoroalkyl and monochloroperfluoroalkyl dichloromethanes being oxidized.

It has been found that $Cl_2$ or HCl are effective catalysts for the initiation of the reaction at lower temperatures and pressures and thus can allow the reduction of the reaction time, temperature or pressure to fit the equipment available. It will be recognized by the skilled artisan that other materials which can serve as a source of HCl or $Cl_2$ under reaction conditions can also be effective, e.g., HCFC-123a, an impurity in commercial HCFC-123, can readily eliminate HCl under reaction conditions. HCl can be then oxidized by oxygen to $Cl_2$ and water.

An increase in the surface to volume ratio in a pipeline reactor has been shown to increase the rate of the reaction. Experiments carried out in a 2"×20" ALLOY C-276 sold under the trademark HASTELLOY® C276 reactor showed a threefold increase in conversion when the reactor was packed with ALLOY 600 sold under the trademark INCONEL® 600 wire mesh compared to an unpacked reactor.

The product perhaloacyl chlorides are isolated by standard procedures such as distillation. Where the product boils below room temperature the distillation may be carried out under pressure. For example, the purification of TFAC may be achieved by distillation under pressure using a 10 plate Oldershaw column or equivalent. A co-product, i.e., side product is HCl. As exemplified hereinafter, by-products depend on the substrate employed.

This invention is an improvement over previous processes for the preparation of TFAC and related compounds in that it avoids the need for a source of active radiation while eliminating the need for water which was previously considered necessary as a catalyst in the non-radiative processes. The presence of water hydrolyses the products to the corresponding acids which are not useful as acylating agents per se for perhaloacylating amines and alcohols to form amides and esters, respectively. This invention provides a method for the production of TFAC and related materials in which the product can be separated readily from side products and unreacted starting materials, in a highly pure form while minimizing corrosive by-products. The process exhibits increased selectivity and conversion to TFAC without the concomitant formation of substantial amounts of TFAA and without the need for active radiation. This is accomplished by carrying out the oxidation within the supercritical region of the reactants and in the absence of water. It will be appreciated by those skilled in the art that the TFAC obtained by the present process can be further hydrolyzed with water to produce TFAA, if desired.

The following examples serve to illustrate the invention, but are not intended to limit the scope of the invention. The following additional abbreviations are used in the examples: trifluoroacetic acid is TFAA, 1,1,1-trichloro-2,2,2-trifluoroethane is F-113a, hexafluoro-2,2,3,3-tetrachlorobutane is FC-316 maa.

All analyses reported in the following Examples were gas chromatography analyses using a Hewlett-Packard Series II 5890 instrument. A 105 m×0.32 mm RTX-1(Restek Corp., Bellefonte, Pa.) capillary column was used with a thermal conductivity detector. A temperature program of 40° C. (15 minute hold), heating 16° C./min to 200° C. (10 minute hold), and heating 50° C./min to 250° C. (10 minute hold) was employed.

"Conversion" and "selectivity" which are used herein are defined as follows. Conversion is molar % of HCFC-123 consumed. Selectivity is defined as:

$$\frac{\text{moles product or by-product}}{\text{moles starting material consumed}} \times 100\%$$

EXAMPLE 1

Commercial grade (>98%) HCFC-123 (41.3 g, 0.27 mole) in a 400 cc Nickel based alloy sold under the trademark HASTELLOY® shaker bomb was charged with 120 psig $O_2$ at room temperature. The contents of the bomb were heated to 220° C. for 15 minutes at 700 psig system pressure. Analysis indicated a 90% conversion of HCFC-123 to TFAC(91%), TFAA(4%), and F-113a(2%).

EXAMPLE 2

A charge of HCFC-123 (152.9 g, 1.0 mole) in the Nickel based alloy sold under the trademark HASTELLOY® shaker bomb was heated to 200° C. Four 130 psig $O_2$ injections from a 300 cc reservoir at 1500 psig were then made at 15 minute intervals to give a final pressure of 1240 psig. The mixture was reacted for one hour. Analysis indicated a 67% conversion of HCFC-123 to TFAC(86%), TFAA(6%), and F-113a(6%).

COMPARATIVE EXAMPLE 2

The same run as in Example 2 was made in a 316 stainless steel autoclave. There was a red-brown coating on the internal surface of the autoclave. Analysis indicated only a 9% conversion of HCFC-123 to TFAC(22%), TFAA(17%), and F-113a(5%).

EXAMPLE 3

HCFC-123 (152.9 g, 1.0 mole) in the Nickel based alloy sold under the trademark HASTELLOY® bomb was charged with 100 psig $O_2$ at room temperature and heated to 200° C. for one hour at 1080 psig system pressure. Analysis indicated a 27% conversion of HCFC-123 to TFAC(78%), TFAA(3%), and F-113a(5%).

COMPARATIVE EXAMPLE 3

The same run as in Example 3 was made with the addition of water (3.6 g, 0.2 mole). Analysis indicated complete recovery of HCFC-123 and no product formation.

This illustrates the inhibitive effect of water under these reaction conditions.

EXAMPLE 4

HCFC-123 (152.9 g, 1.0 mole) in a 400 cc ALLOY 600 sold under the trademark INCONEL® 600 bomb was charged with 100 psig $O_2$ and heated to 200° C. for 30 minutes at 1125 psig system pressure. Analysis indicated a 28% conversion of HCFC-123 to TFAC(85%), TFAA(6%), and F-113a(5%).

EXAMPLE 5

HCFC-123 (152.9 g, 1.0 mole) in a 400 cc silver clad bomb was charged with 100 psig $O_2$ and heated to 200° C. for five hours at 945 psig system pressure. Analysis indicated a 20% conversion of HCFC-123 to TFAC(87%), TFAA(6%), and F-113a(6%).

EXAMPLE 6

HCFC-123 (152.9 g, 1.0 mole) in a 400 cc tantalum bomb was charged with 100 psig $O_2$ at room temperature and heated to 200° C. for one hour at 880 psig system pressure. Analysis indicated at 15% conversion of HCFC-123 to TFAC(82%), TFAA(8%), and F-113a(7%).

EXAMPLE 7

HCFC-123 (152.9 g, 1.0 mole) in a 400 cc nickel bomb was charged with 100 psig $O_2$ at room temperature and heated to 200° C. for five hours at 860 psig system pressure. Analysis indicated a 15% conversion of HCFC-123 to TFAC(64%), TFAA(10%), and F-113a(16%).

EXAMPLE 8

$CF_2ClCHCl_2$ (HCFC-122; 169.4 g, one mole) was heated to 250° C. in a 400 cc Nickel based alloy sold under the trademark HASTELLOY® autoclave. Three 100 psig injections of $O_2$ were made into the autoclave from a 300 cc $O_2$ reservoir at 1500 psig pressure at 30 minute intervals. After the final injection at 1 hour and 30 minutes the reaction was continued an additional 30 minutes for a total reaction time of two hours at 1555 psig system pressure. Analysis of the final solution by gas chromatography indicated a 41% conversion of HCFC-122 to $CF_2ClCOCl$(32%), $CF_2ClCCl_3$(9%), $CF_2ClCOOH$(4%), $CF_3COCl$(5%), and $COCl_2$(3%).

EXAMPLE 9

$ClCF_2CF_2CHCl_2$ (HCFC-224 ca; 136.6 g, 0.62 mole) was heated to 250° C. in a 400 cc Nickel based alloy sold under the trademark HASTELLOY® autoclave. Four-100 psig injections of $O_2$ were made from a 300 cc $O_2$ reservoir at 1500 psig to give a system pressure of 820 psig. The mixture was reacted for two hours. Analysis of the solution indicated a 44% conversion of HCFC-224 ca to $ClCF_2CF_2COCl$(72%), $ClCF_2CF_2CCl_3$(19%), $CF_3CF_2Cl$(4%), and $COCl_2$(3%).

EXAMPLE 10

$CF_3CF_2CHCl_2$ (HCFC-225 ca; 202.8 g, one mole) was heated to 280° C. in a 400 cc nickel based alloy sold under the trademark HASTELLOY® autoclave. Two 150 psig injections of $O_2$ were made from a 300 cc $O_2$ reservoir at 1600 psig at a 60 minute interval. After the final injection, the reaction was continued for an additional hour for a total reaction time of two hours under 1380 psig total pressure. Analysis of the solution indicated a 33% conversion of HCFC-225 ca to $CF_3CF_2COCl$(59%), $CF_3CF_2CCl_3$(16%), $CF_3CF_2COOH$(21%), and $COCl_2$(3%).

EXAMPLES 11-25

The following examples, Examples 11-27, were carried out in a continuous fashion in a pipeline reactor. The general procedure was as follows. A 40 ft.×0.5 in. pipeline reactor was immersed into a eutectic salt bath heated to the desired temperature (200°-320° C.) and the reactant was fed through a static mixer at a predetermined rate with an Eldex Model B-100S (San Carlos, Calif.), feed pump along with oxygen (as air) to the reactor entrance. The air flow was controlled and measured with a Brooks Model 5850E (Brook Instrument Division, Emerson Electric, Hatfield, Pa.) mass flow controller. The standard procedure was to heat the reactor to the desired temperature, turn on the feed streams, and then regulate the pressure using a valve at the end of the reactor.

The reaction products were condensed in a cooled vessel and the desired fraction isolated by distillation through a pressure distillation column. The vessel contents can be analyzed by gas chromatography, as described above.

Examples 11-20 and 26-27 were carried out in a continuous fashion as above in a AALOY C-276 sold under the trademark HASTELLOY® C276 reactor by feeding HCFC-123 and air. Experiments 21-25 were carried out in an ALLOY 600 sold under the trademark INCONEL® 600 reactor. The excess oxygen refers to the amount of oxygen in air in excess of the HCFC-123/oxygen stochiometric ratio of 1.0/0.5. The principal by-products in these runs were FC-113a, TFAA, FC-316maa, and phosgene.

TABLE 1

| Ex. | T °C. | Press. (psig) | xs $O_2$ (%) | Time (min) | Conv (%) | Selec (%) (TFAC) |
|---|---|---|---|---|---|---|
| 11 | 230 | 1000 | 5 | 15 | 83 | 96 |
| 12 | 250 | 1000 | 50 | 15 | 99 | 95 |
| 13[1] | 250 | 1000 | 50 | 15 | 99 | 95 |
| (comparison to 12, water has no effect at low levels) | | | | | | |
| 14 | 250 | 700 | 50 | 15 | 94 | 93 |
| 15 | 250 | 1000 | 50 | 5 | 98 | 97 |
| 16 | 240 | 1000 | 100 | 5 | 96 | 95 |
| 17 | 275 | 1000 | 100 | 5 | 99 | 94 |
| 18 | 230 | 1040 | 50 | 5 | 0 | 0 |
| 19[2] | 230 | 1040 | 50 | 5 | 15 | 91 |
| (comparison to 18, initiator required at lower temp. and short residence time) | | | | | | |
| 20 | 230 | 1300 | 50 | 10 | 95 | 95 |
| 21 | 240 | 1000 | 50 | 10 | 97 | 99 |
| 22 | 250 | 1000 | 50 | 5 | 95 | 96 |
| 23 | 250 | 700 | 50 | 15 | 82 | 95 |
| 24 | 230 | 1040 | 50 | 5 | 0 | 0 |
| 25[3] | 230 | 1040 | 50 | 5 | 28 | 91 |
| (comparison to 24, initiator required at lower temp. and short residence time) | | | | | | |

[1]Dried over a silica-alumina dessicant to lower the water content from 100 ppm to less than 5 ppm. Shows water is not required.
[2]0.22 g HCl/100 g HCFC-123 added to HCFC-123 feed as initiator.
[3]0.22 g $Cl_2$/100 g HCFC-123 added to HCFC-123 feed as initiator.

EXAMPLES 26

Using a 2 in.×20 in. ALLOY C-276 sold under the trademark HASTELLOY® C276 reactor at 250° C. and 1000 psig, 50% excess oxygen and 5 minute residence time the conversion of HCFC-123 was 26% with 90% selectivity to TFAC.

EXAMPLE 27

Using the same procedure as Example 26 except the reactor was packed with ALLOY 600 sold under the trademark INCONEL® 600 wire mesh to give a surface area to volume ratio of 600 ft-1, the conversion increased to 70% and the selectivity was 92%. This example illustrates the advantage of increased surface area.

What is claimed is:

1. A process for preparing perhaloacyl chlorides of the formula $X(CF_2)_nCOCl$ comprising contacting compounds of formula $X(CF_2)_nCHCl_2$ with oxygen in the absence of water within the supercritical region of said compounds
wherein
X=F or Cl and
n=1-4.

2. The process of claim 1 wherein X=F and n=1 and the temperature is between 220° and 300° C. and the pressure is from 700 to 1400 psig.

3. The process of claim 1 or claim 2 wherein the process is operated continuously using dry air as an oxygen source.

4. A continuous process for preparing trifluoroacetyl chloride comprising oxidizing 1,1 dichloro-2,2,2-trifluoroethane with dry air as a source of oxygen in a pipeline reactor at a temperature of 220°–300° C., at a total pressure of 700–1400 psig and a time of 3–15 minutes in the absence of water, wherein the 1,1-dichloro-2,2,2-trifluoroethane to oxygen stoichiometric ratio is 1.0/0.5 to 1.0/1.0.

5. The process of claim 3, further comprising, catalytic amounts of chlorine of HCl wherein said chlorine or HCl are used as an initiator.

6. The process of claim 4, further comprising, catalytic amounts of chlorine or HCl wherein said chlorine or HCl are used as an initiator.

* * * * *